(12) United States Patent
Luescher et al.

(10) Patent No.: US 7,053,049 B2
(45) Date of Patent: May 30, 2006

(54) METHOD FOR TREATING UNSTABLE ANGINA PECTORIS

(75) Inventors: Thomas Luescher, Zumikon (CH); Georg Noll, Erlenbach (CH); Peter Lerch, Bern (CH)

(73) Assignee: ZLB Behring AG, Bern (DE)

( * ) Notice: Subject to any disclaimer, the term of this patent is extended or adjusted under 35 U.S.C. 154(b) by 255 days.

(21) Appl. No.: 10/333,212

(22) PCT Filed: Jul. 20, 2001

(86) PCT No.: PCT/EP01/08425

§ 371 (c)(1),
(2), (4) Date: Aug. 18, 2003

(87) PCT Pub. No.: WO02/07753

PCT Pub. Date: Jan. 31, 2002

(65) Prior Publication Data

US 2004/0014654 A1    Jan. 22, 2004

(30) Foreign Application Priority Data

Jul. 20, 2000 (DE) ............................... 100 35 352

(51) Int. Cl.
*A61K 38/17* (2006.01)
(52) U.S. Cl. ............................ 514/12; 514/2; 530/359
(58) Field of Classification Search .................. 514/2, 514/12; 530/359
See application file for complete search history.

(56) References Cited

U.S. PATENT DOCUMENTS 5,089,602 A * 2/1992 Isliker et al. ............... 530/359
5,128,318 A   7/1992 Levine et al.
5,652,339 A * 7/1997 Lerch et al. ................ 530/359

FOREIGN PATENT DOCUMENTS

WO    WO 01/13939    3/2001
WO    WO 01 38395    5/2001

OTHER PUBLICATIONS

Tsutsumi et al., "The Novel Compound NO-1886 Increases Lipoprotein Lipase Activity with Resulting Elevation of High Density Lipoprotein Cholesterol . . . ," J. Clin. Invest., vol. 92, Jul. 1993, pp. 411-417.*

Paul Dimayuga et al., "Reconstituted HDL Containing Human Apolipoprotein A-1 Reduces VCAM-1 Expression and Neointima Formation Following Periadventitial Cuff-Induced Carotid Injury in apoE Null Mice", Biochemical and Biophysical Research Communications (1999), 264(2), 465-468, XP002218783.

Lukas E. Spieker et al., "High-density liproprotein restores endothelial function in hypercholesterolemic men." Circulation, (Oct. 31, 2000), vol. 102, No. 18, Supplement, pp. II.315-II.316.

P.G. Lerch et al., "Reconstituted high density lipoprotein (rHDL) modulates platelet activity in vitro and ex vivo", Thrombosis and Haemostasis, (Aug. 1998) 80(2) 316-20 XP008009389.

R. Moudry et al., "Reconstituted high density lipoprotein modulates adherence of polymorphonuclear leukocytes to human endothelial cells", Shock (Mar. 1997) 7 (3) 175-81 XP008009425.

* cited by examiner

Primary Examiner—Robert A. Wax
(74) Attorney, Agent, or Firm—Millen, White, Zelano & Branigan, P.C.

(57) ABSTRACT

The invention relates to the use of reconstituted HDL for improving the endothelial function in patients suffering from hypercholesterolaemia and for treating or preventing acute coronary diseases such as unstable angina pectoris.

15 Claims, 3 Drawing Sheets

METHOD FOR TREATING UNSTABLE ANGINA PECTORIS

Figure 1:
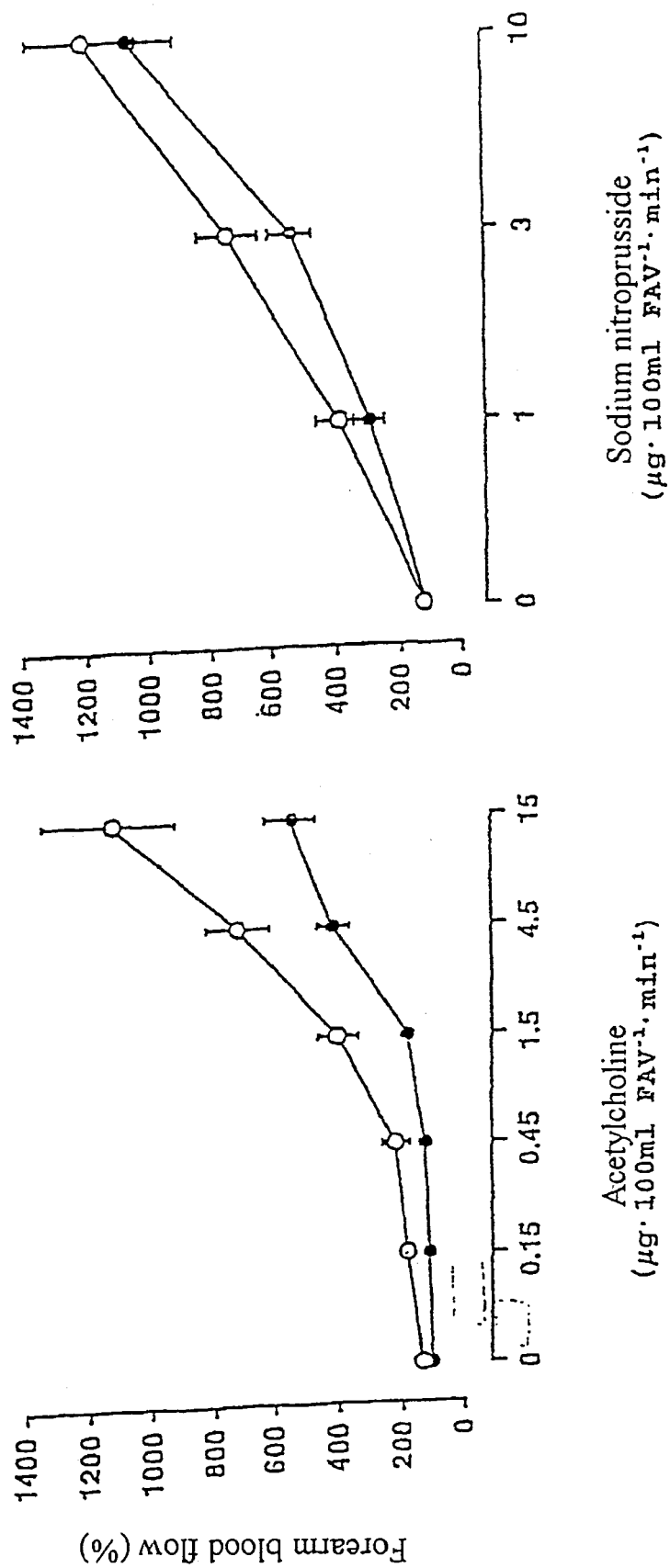

The invention relates to the use of reconstituted HDL for improving endothelial function in hyper-cholesterolemia and for the therapy or prophylaxis of acute coronary disorders such as unstable angina pectoris or myocardial infarction.

The endothelium on the one hand separates the blood from extravascular tissue, and on the other hand regulates important functions of the vessel wall. An important prerequisite for the endothelial monolayer to function fully is its functional and structural integrity. Some of the important functions of the endothelium are control of the adhesion of cells (monocytes, platelets), the invasion of immunocompetent cells and the proliferation of smooth muscle cells. In addition, bioactive substances such as prostaglandins, nitric oxide (NO) or endothelin-1 are produced in the endothelial cells. These substances have effects on the structure, the metabolism and the permeability of vessels, modulate vascular tone and control coagulation, fibrinolysis and inflammatory reactions.

Injury to the endothelium or inflammations, for example caused by unfavorable lipid profiles, lead to dysfunction, a critical factor in the development of atherosclerosis. This process may take place over years or decades and does not in the early stage lead to any clinical symptoms. However, with suitable methods, it is possible to find structural changes in the vessel wall in this stage. High cholesterol levels, especially high LDL cholesterol, or low HDL cholesterol favors rapid buildup of atherosclerosis, which normally starts with deposits in the form of fatty streaks which may later develop into plaques. Such plaques may lead to local reductions in blood flow or, if there is increased mechanical stress, also rupture, form thrombi and lead to acute coronary syndromes such as unstable angina pectoris or myocardial infarction. Unstable angina pectoris is also described as an inflammatory reaction which leads to a systematic dysfunction of endothelial cells.

The therapy of acute coronary syndromes attempts to restore or replace the inadequate function of endothelial cells. This means aiming for coronary vasodilatation, an inhibition of platelets, an inhibition of coagulation or revascularization (bypass, PTCA/stenting). Pharmaceutical agents used for this purpose are GP IIb-IIIa antagonists, heparin, Cox inhibitors or NSAIDs (aspirin), beta blockers and nitrates. It is attempted in the long term to lower the plasma cholesterol level. With aggressive therapy it is normally possible to stabilize acute coronary syndromes within 48 hours.

As already mentioned, a reduced HDL chlolesterol level is a risk factor which may lead to atherosclerosis or acute coronary syndromes. It is assumed that HDL conveys, with the so-called reverse cholesterol transport, excess cholesterol from the periphery into the liver, where cholesterol is processed to bile acids and subsequently excreted with the bile. If plasma HDL concentrations are reduced, cholesterol is eliminated too slowly and may be deposited in vessel walls.

Endothelial function can be measured in vivo by various methods. The coronary circulation can be quantitated by catheterization and new imaging techniques. Measurement of the circulation in the forearm is better and more easily accessible. Although no lesions are normally observed in the vessels there, it is possible with this method to observe even small changes in vascular functions. Plethysmography can be used to determine small changes in blood flow on stimulation with acetylcholine. New, noninvasive ultrasound systems can be used to determine the diameter of arteries accurately and thus to check and assess vascular function.

Reconstituted HDL can be obtained from plasma, apolipoprotein A-I and soybean lecithin. Methods for obtaining reconstituted HDL (rHDL) are described for example in Circulatory Shock 40 (1993), 14–23, or in the U.S. Pat. Nos. 5,089,602, 5,128,318 and 5,652,339. rHDL binds to lipids or lipid-like substances, for example lipopolysaccharides of Gram-negative bacteria in the blood and can thus be employed for the treatment of septic shock.

An abstract by Newton (Workshop: New Aspects of Pharmacological Treatment, June 2000) discloses that a favorable effect was found in animal models of restenosis and arteriosclerosis after administration of rHDL. The treatment of acute and chronic vascular disorders in humans is, by contrast, referred to expressly as "unresearched area". There is thought to be a possible benefit for reverse cholesterol transport on administration of rHDL, but this is of no importance for controlling an acute disorder such as unstable angina pectoris. There is thus no evidence that rHDL could be used for the short-term stabilization of acute coronary syndromes. Sirtori (Workshop: New Aspects of Pharmacological Treatment, June 2000) proposes the use of apolipoprotein mutants and mimetics for the treatment of vascular disorders. It is reported that administration of rHDL inhibits atherosclerosis, intimal proliferation and restenosis in several animal models, and improves endothelial function in an animal model, the apoE KO mouse. However, data obtained in animal models cannot be applied directly to humans because of the differences, some of which are considerable, in lipoprotein metabolism in rodents and humans. It is moreover not possible in the current state of the art to simulate complex disorders of the coronary vessels, such as angina pectoris in animal models. In addition, there is no evidence at all that administration of rHDL might have a short-term effect in acute coronary disorders.

In the investigations leading to the present invention, rHDL was administered to patients with an elevated plasma cholesterol level and thus an increased risk of acute coronary syndromes such as unstable angina pectoris or myocardial infarction. During the infusion of rHDL, endothelial function was followed in the forearm circulation of the patients. It was surprisingly found in this connection that a very rapid acute improvement in a previously impaired endothelial function can be achieved after infusion of rHDL. This acute effect observed for rHDL is unexpected and is not explicable by or compatible with current ideas about the biological effect of rHDL in reverse cholesterol transport. Thus, an infusion of rHDL is unable within the short experimental period of a few hours to reverse the effects, which have built up over decades, of atherosclerosis such as fatty streaks or plaques. It is assumed rather that a previously unknown acute systemic effect is involved and is able very rapidly to improve the impaired dysfunction of endothelial cells, and thus can be utilized for the treatment and/or prophylaxis of coronary disorders, especially unstable angina pectoris or myocardial infarction.

The advantages of therapy of acute coronary syndromes with rHDL are a rapid improvement in endothelial function which results in a favorable effect on several clinically relevant parameters. In addition, a permanent effect might occur through attainment of a favorable influence on the lipid profile. rHDL is moreover a body-like substance so that the treatment is substantially without side effects. It is assumed that the effect of rHDL is based on an improved bioavailability of NO in the vessel wall, which leads to inhibition of platelet adhesion and-aggregation, and relaxes vascular tone.

It is possible in patients with acute coronary disorders such as, for example, unstable angina pectoris to achieve a smaller incidence of secondary complications after one or more infusions of rHDL.

Unstable angina pectoris is a clinical syndrome of myocardial ischemia which is characterized by anginal chest pain at rest with ECG changes. Differentiation from myocardial infarction is effected by biochemical markers of myocardial damage (CK, CK-MB) and ECG.

One aspect of the present invention is thus the use of reconstituted HDL for producing an agent for improving endothelial function, in particular an agent for improving acute endothelial function in vascular disorders, e.g. the acute function of the coronary endothelium, especially in human medicine.

A further aspect of the invention is the use of reconstituted HDL for producing an agent for the prophylaxis or/and treatment of acute coronary disorders such as, for example, unstable angina pectoris or myocardial infarction. rHDL can be employed for example for pathological states such as non-Q wave infarction and acute coronary disorders either with, or without, slightly elevated or highly elevated troponin T level. rHDL is particularly preferably employed for improving endothelium-dependent vasodilatation in human patients.

It is favorable to administer rHDL by infusion, e.g. by arterial, intraperitoneal or, preferably, intravenous infusion in a dosage of from 10 to 150 mg, preferably 40 to 80 mg per kg of bodyweight per treatment. The administered dose can be infused for example in an amount of from 20 to 100 mg, in particular 20 to 80 mg, of rHDL, corresponding to 0.04 to 0.6 mg of rHDL per min (dose based on protein) for a time of from 10 min to several hours. It is possible where appropriate for the rHDL infusion to be repeated one or more times if required.

The administered rHDL contains apolipoprotein A-I and phospholipid, e.g. phosphatidylcholine, preferably in a molar ratio of from 1:50 to 1:250, particularly preferably in a ratio of about 1:150, and may additionally contain further lipids such as, for example, cholesterol, preferably up to a molar ratio of 1:20, e.g. 1:5 to 1:20 (relative to the apolipoprotein).

The rHDL administration can be combined with administration of other therapeutic agents such as, for example, GP IIb–IIIa antagonists, e.g. antibodies such as RheoPro, Integrilin or tirofiban, heparin, COX inhibitors or NSAIDs such as aspirin, beta blockers or nitrates. Combined administration with heparin or/and aspirin is particularly preferred.

Finally, the invention relates to a method for the prophylaxis or/and treatment of acute coronary disorders or coronary syndromes such as, for example, unstable angina pectoris or myocardial infarction, wherein rHDL is administered. The administration to a subject, preferably a human patient, takes place in such a way that rHDL is administered in an amount sufficient to alleviate or eliminate acute coronary syndromes, in a suitable form, for example by infusion.

The invention is to be further explained by the following figures and examples. These show:

FIG. 1: The reactions of the forearm blood flow to intraarterial infusion of acetylcholine or sodium nitroprusside in normal or hypercholesterolemic people. The endothelium-dependent vasodilatation with acetylcholine is significantly inhibited (p<0.0001) in hypercholesterolemic people (filled circles) compared with healthy subjects (open circles). The endothelium-independent vasodilatation with sodium nitroprusside is comparable in both groups.

Figure 2:
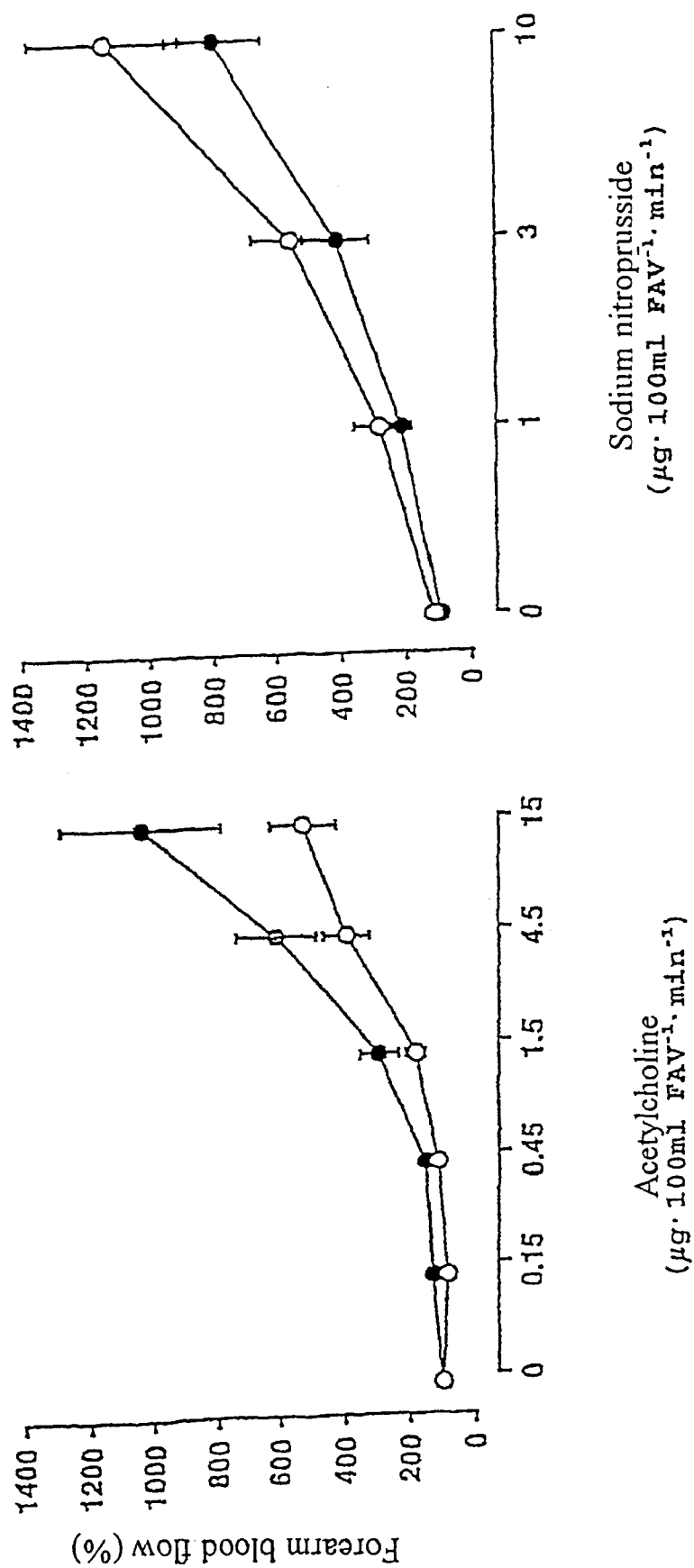

FIG. 2: The endothelium-dependent and -independent vasodilatation with acetylcholine or sodium nitroprusside in hypercholesterolemic people before (open circles) or after (filled circles) intravenous infusion of reconstituted HDL. There is a significant improvement (p=0.017) in the endothelium-dependent vasodilatation with acetylcholine, but not with sodium nitroprusside, an endothelium-independent vasodilator.

Figure 3:
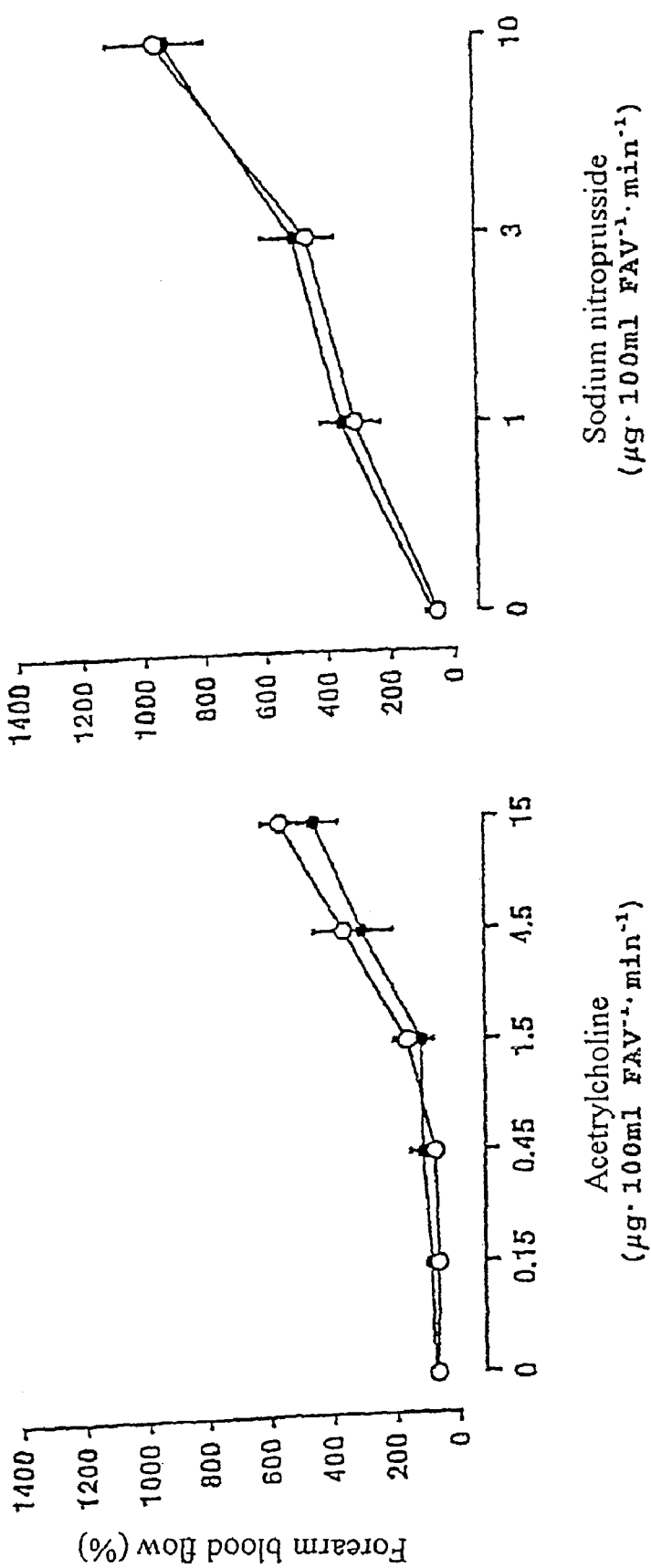

FIG. 3: The endothelium-dependent and -independent vasodilatation after administration of acetylcholine or sodium nitroprusside in hypercholesterolemic patients before (open circles) and after (filled circles) intravenous infusion of reconstituted HDL during inhibition of NO synthase with L-NMMA. There is no significant change in the reactions to intraarterial infusions with acetylcholine or sodium nitroprusside.

EXAMPLE 1

1. Methods 1.1 Patients 18 healthy hypercholesterolemic men with a plasma LDL cholesterol concentration of >155 mg/dl (>4.0 mmol/l) and 8 healthy normocholesterolemic men with an LDL cholesterol content of <135 mg/dl (<3.5 mmol/l) took part in the study. The criteria for exclusion were arterial hypertension ($\geq$140/90 mmHg), diabetes mellitus and smoking.

The patients took no food, alcohol or caffeine during the 12 hours preceding the study. A statin therapy of two patients was discontinued four weeks before the experiment, and none of the other people took lipid-lowering agents or other agents.

1.2 Protocol

The forearm blood flow (lower arm blood flow) was determined simultaneously in both arms by venous occlusion plethysmography (EC-4, Hokanson) (Benjamin et al, Hypertension 25 (1995), 918–923). The people lay stretched out with arms slightly raised above the level of the heart in order to improve venous drainage. Circulation in the hand was prevented by wrist bandages with a suprasystolic pressure (220 mmHg) one minute before the measurements (Kerslake, J. Physiol. 108 (1949), 451–457). To determine the endothelium-dependent and -independent vasodilatation, acetylcholine (Miochol E, Ciba Vision, Switzerland) and sodium nitroprusside (Nipruss, Schwarz Pharma, Germany) were infused into the brachial artery in increasing amounts of 0.15, 0.45, 1.5, 4.5 and 15 µg×100 ml of forearm volume $(FAV)^{-1} \times min^{-1}$ (each in 0.9% NaCl for 5 minutes) and 1.3 and 10 µg×100 ml $FAV^{-1} \times min^{-1}$ (in 5% glucose for 3 minutes) at a constant rate by an infusion pump through a catheter introduced under local anesthesia. There was an interval of 30 minutes between each of the intraarterial infusions. The signals were recorded by a computer (PowerBook G3; Apple Macintosh) using an analog/digital board (National Instruments) and a modified commercial data acquisition software (LabView, National Instruments).

In hypercholesterolemic volunteers, reconstituted HDL particles (rHDL, ZLB Bioplasma AG, Berne, Switzerland; n=7) containing apolipoprotein A-I and phosphatidylcholine in a ratio of 1:154 or albumin (5%, likewise from ZLB; n=5) were infused intravenously in an equivalent protein dosage of 80 mg/kg for four hours (Lerch et al, Vox Sang 71 (1996), 155–164; Pajkrt et al, J. Exp. Med. 184 (1996), 1601–1608;

Pajkrt et al, Thromb. Haemostat. 77 (1997), 303–307). The infusions of acetylcholine and sodium nitroprusside were then repeated.

In 5 further hypercholesterolemic men, the effects of intravenous rHDL infusion on acetylcholine- and sodium nitroprusside-induced vasodilatation were determined during intraarterial coinfusion of $N^G$-monomethyl-L-arginine (L-NMMA, 4 μmol/min; Clinalfa), an inhibitor of NO synthase. The intraarterial blood pressure and the pulse were recorded continuously.

1.3 Biochemical Analyses

Blood samples were taken before or after infusion of rHDL and albumin. Total cholesterol, HDL cholesterol, triglycerides, liver transaminases and insulin were determined by standard laboratory methods. The LDL cholesterol content was calculated using the Friedewald formula (Friedewald et al, Clin. Chem. 18 (1972), 499–502).

1.4 Statistical Analysis

The results are reported as means±standard deviation (SD). The average values for the forearm blood flow were obtained from at least three consecutive recordings during the last minute of drug infusion. They are reported as percentage ratio of the infused to the non-infused arm, in order to take account of changes in the blood flow caused by systemic factors. Plethysmography measurements were compared using two-way ANOVA for repeated measurements (Wallenstein and Zucker, Circ. Res. 47 (1980), 1–9). The clinical data were compared by the paired or unpaired Student's T test (StatView 4.5, Abacus concept). Statistical significance was assumed with P<0.05.

2. Results

The clinical characteristics of the participants in the study are shown in table 1. The hypercholesterolemic and normocholesterolemic study groups differed only in the lipid concentrations and the body mass index. There was no difference in the basal forearm blood flow in the two groups. The vasodilatory reaction to acetylcholine, but not to nitroprusside, was significantly reduced in the hypercholesterolemic men (FIG. 1).

The effects of rHDL and albumin infusions on the laboratory parameters and hemodynamic parameters of the hypercholesterolemic men are shown in table 2. There were no statistically significant differences between the two hypercholesterolemic groups receiving rHDL or albumin. The intravenous cholesterol-free rHDL infusion led to a significant increase in the plasma HDL cholesterol concentration, but not in the LDL cholesterol, triglyceride or insulin plasma concentration. The endothelium-dependent vasodilatation after administration of acetylcholine was significantly increased by rHDL infusion, whereas the endothelium-independent vasodilatation with sodium nitroprusside remained unchanged (FIG. 2 and tab. 3).

The rHDL-induced improvement in the vasodilatation with acetylcholine was prevented by simultaneous intraarterial infusion of L-NMMA (FIG. 3 and tab. 3).

The endothelium-independent vasodilatation with sodium prusside was unaffected by L-NMMA. L-NMMA led to a significant reduction in the basal forearm blood flow in hypercholesterolemic people (−23±3%). The vasodilatory reactions to acetylcholine and sodium nitroprusside did not differ significantly in the L-NMMA infusion group compared with the hypercholesterolemic group without simultaneous L-NMMA infusion.

Albumin infusion did not influence the vasodilatory reaction either to acetylcholine or to sodium nitroprusside (tab. 3). Other laboratory parameters were also unaffected (tab. 2). No side effects were found. There were also no significant changes in the arterial blood pressure or in the pulse during the study period. The blood flow in the non-infused control arm was not changed by the intraarterial infusions. In both the rHDL and the albumin group there was a distinct but not statistically significant increase in the basal forearm blood flow during the 6 hours the experiments lasted (tab. 3).

TABLE 1

Clinical characteristics and laboratory values

|  | Normocholesterolemic test subjects (n = 8) | Hypercholesterolemic test subjects (n = 18) |
|---|---|---|
| Age (years) | 50 ± 10 | 58 ± 9 |
| Body mass index (kg · m$^{-2}$) | 22.9 ± 1.7 | 26.4 ± 2.7* |
| Systolic blood pressure (mmHg) | 118 ± 9 | 127 ± 11 |
| Diastolic blood pressure (mmHg) | 70 ± 5 | 73 ± 16 |
| Heart rate (beats per minute) | 56 ± 6 | 66 ± 13 |
| Basal FBF (ml · 100 ml FAV$^{-1}$ · min$^{-1}$) | 2.6 ± 0.7 | 2.8 ± 1.1 |
| Total cholesterol (nmol/l) | 4.8 ± 0.7 | 7.1 ± 0.9† |
| HDL cholesterol (mmol/l) | 1.6 ± 0.5 | 1.4 ± 0.3 |
| LDL cholesterol (mmol/l) | 2.8 ± 0.7 | 5.0 ± 0.7† |
| Triglycerides (mmol/l) | 0.8 ± 0.2 | 1.6 ± 0.7* |
| Glucose (mmol/l) | 4.8 ± 0.8 | 5.0 ± 0.4 |
| ALAT (U/l) | 24 ± 8 | 30 ± 13 |

Values are means ± SD
FBF means forearm blood flow, FAV forearm blood volume and ALAT alanine aminotransferase.
*P < 0.01, †P < 0.0001

TABLE 2

Effect of infusions on the characteristics of hypercholesterolemic test subjects

|  | rHDL (n = 12) | | Albumin (n = 5) | |
|---|---|---|---|---|
|  | pre | post | pre | post |
| Age (years) | 55 ± 3 | — | 58 ± 4 | — |
| Body mass index (kg · m$^2$) | 27 ± 1.2 | — | 26.0 ± 1.1 | — |
| Systolic blood pressure (mmHg) | 123 ± 2 | 123 ± 1 | 121 ± 11 | 123 ± 11 |
| Diastolic blood pressure (mmHg) | 61 ± 3 | 61 ± 3 | 62 ± 4 | 64 ± 6 |
| Pulse (min$^{-1}$) | 64 ± 3 | 66 ± 3 | 60 ± 5 | 57 ± 5 |
| Total cholesterol (mmol/l) | 6.7 ± 0.3 | 7.4 ± 0.3 | 6.5 ± 0.4 | 6.4 ± 0.4 |
| HDL cholesterol (mmol/l) | 1.2 ± 0.0 | 2.1 ± 0.1* | 1.4 ± 0.1 | 1.4 ± 0.1 |
| LDL cholesterol (mmol/l) | 5.2 ± 0.3 | 4.9 ± 0.2 | 4.5 ± 0.3 | 4.5 ± 0.4 |
| Triglycerides (mmol/l) | 1.5 ± 0.2 | 2.1 ± 0.3 | 1.2 ± 0.2 | 1.2 ± 0.2 |
| Insulin (pmol/l) | 66 ± 14 | 63 ± 11 | 76 ± 15 | 62 ± 10 |
| Glucose (mmol/l) | 5.0 ± 0.2 | — | 5.1 ± 0.2 | — |
| Alanine aminotransferase (U/l) | 18 ± 1.3 | 18 ± 1.3 | — | — |

Values are means ± SD
FBF means forearm blood flow, FAV forearm blood volume
*P < 0.0001 compared with corresponding pre-infusion value

TABLE 3

Effect of various agents on the forearm blood flow in hypercholesterolemic men

| | | rHDL (80 mg/kg, n = 7) | | Albumin (80 mg/kg, n = 5) | | L-NMMA +rHDL (80 mg/kg, n = 5) | |
|---|---|---|---|---|---|---|---|
| | | pre | post | pre | post | pre | post |
| Baseline | | 3.0 ± 0.5 | 3.3 ± 0.5 | 2.7 ± 0.5 | 3.3 ± 0.8 | 2.0 ± 0.3 | 2.3 ± 0.3 |
| Acetylcholin | 0.15 | 3.2 ± 0.6 | 4.5 ± 0.6* | 3.4 ± 0.7 | 3.5 ± 0.5 | 1.9 ± 0.3 | 2.1 ± 0.2 |
| (μg/min/100 ml FAV) | 0.45 | 3.5 ± 0.5 | 4.6 ± 0.6* | 3.4 ± 0.6 | 3.8 ± 0.6 | 2.0 ± 0.2 | 2.0 ± 0.3 |
| | 1.5 | 6.2 ± 1.9 | 9.3 ± 2.0* | 5.6 ± 1.7 | 7.0 ± 2.0 | 3.9 ± 1.0 | 3.4 ± 1.2 |
| | 4.5 | 11.6 ± 2.7 | 17.8 ± 2.8* | 12.9 ± 4.2 | 14.4 ± 5.3 | 8.4 ± 2.2 | 7.5 ± 2.3 |
| | 15 | 14.8 ± 3.0 | 28.3 ± 4.3* | 17.6 ± 6.4 | 20.6 ± 9.1 | 12.2 ± 1.3 | 11.1 ± 1. |
| Baseline | | 3.2 ± 0.4 | 3.7 ± 0.5 | 2.7 ± 0.3 | 2.5 ± 0.2 | 1.7 ± 0.2 | 2.2 ± 0.3 |
| Nitroprusside | 1 | 5.9 ± 1.0 | 7.5 ± 0.9 | 9.2 ± 1.8 | 8.0 ± 1.4 | 8.5 ± 2.4 | 12.4 ± 3. |
| (μg/min/100 ml FAV) | 3 | 10.7 ± 1.7 | 13.2 ± 2.0 | 14.4 ± 2.8 | 15.3 ± 2.6 | 12.0 ± 3.3 | 13.9 ± 3. |
| | 10 | 22.2 ± 2.2 | 25.6 ± 2.2 | 23.9 ± 3.3 | 22.1 ± 4.1 | 20.5 ± 2.2 | 19.7 ± 2. |

Values are means ± SD of the forearm flow
*P < 0.05 for pre compared with post

EXAMPLE 2

1. Methods 1.1 Patients

Patients with unstable angina pectoris (Braunwald classification IIIb) after acute treatment had taken place, i.e. 3–5 days after hospitalization, took part in the study. The patients were between 20 and 75 years of age.

1.2 Protocol

The forearm blood flow is determined simultaneously on both arms by venous occlusion plethysmography. This entails venous blood outflow being prevented on the upper arm with a blood pressure cuff pumped to 40 mm Hg, so that only blood can flow into the arm—but not out. The increase brought about thereby in the forearm circumference is measured by an expansion-sensitive rubber belt. Circulation in the hand is temporarily stopped with a wrist cuff. The signals are recorded as described in example 1.

The endothelium-dependent and -independent vasodilatation is measured by infusing acetylcholine and sodium nitroprusside, respectively, as described in example 1.

A GE advance PET tomograph (GE Medical Systems, Milwaukee, Wis.) with an axial visual field of 35×4.25 mm is used for the positron emission tomography (PET). 700–900 MBq of $^{13}$N-ammonia or $^{15}$O-water are administered to the volunteers by bolus injection into a peripheral vein, while serial transaxial tomographic images of the heart are recorded (frame: 12×10 s, 4×30 s, 1×60 s and 2×30 s). After recording for 20 minutes, a 20-minute transmission scan is carried out for photon attenuation correction using external $^{68}$Ge sources. The myocardial blood flow (MBF) is measured at rest and under standard stress conditions, i.e. administration of adenosine (0.14 mg/kg/min for 7 minutes).

The heart is divided into 16 segments in accordance with the recommendations of the American Society of Echocardiography. The left ventricular blood flow is also investigated.

The MBF is determined by a method described by Muzik et al. (J. Nucl. Med. 34 (1993), 83–91) and subjected to a correction described by Hutchins (J. Am. Coll. Cardiol. 15 (1990), 1032–1042) and Hutchins et al. (J. Nucl. Med. 33 (1992), 1243–1250). The coronary flow reserve (CFR) is calculated as the ratio between the hyperemic and resting MBF values. The reproducibility of this method is confirmed by Kaufmann et al. (J. Nucl. Med. 40 (1999), 1848–1856) and Wyss et al. (Eur. Heart J. 21 (2000), 568).

After an initial measurement of the endothelial function by means of plethysmography and positron emission tomography, rHDL is intravenously infused in a dosage of 80 mg/kg for 4 hours, and the endothelial function is measured a second time. Blood pressure and heart rate are recorded continuously.

The invention claimed is:

1. A method for treating vascular disorders for the acute improvement of endothelial function, comprising:
administering an amount of reconstituted HDL which is sufficient for the acute improvement of endothelial cell function in a vascular disorder.

2. The method of claim 1, wherein said vascular disorder is unstable angina pectoris or myocardial infarction.

3. The method of claim 1, wherein the rHDL is administered by infusion.

4. The method of claim 3, wherein intravenous infusion takes place.

5. The method of claim 1, wherein 10–150 mg of rHDL (weight based on the apolipoprotein) are administered per kg of body weight per treatment.

6. The method of claim 5, wherein the administered dose is infused in an amount of from 0.04 to 0.6 mg of rHDL (weight based on the apoliprotein) per mm for a time of from 10 mm to several hours.

7. The method of claim 1, wherein the administered rHDL has a molar ratio of apolipoprotein A-I to phospholipids in the range from 1:50 to 1:250, and optionally comprises additional lipids such as cholesterol in a molar ratio of up to 1:20 to the apolipoprotein.

8. The method of claim 1, wherein the administration of rHDL is combined with administration of other therapeutic agents.

9. The method of claim 1, wherein the administered HDL results in a measurable improvement in endothelial function during HDL infusion.

10. The method of claim 1, wherein the amount of HDL administered is determinable by an improvement in endothelial function during HDL infusion.

11. The method of claim 1, wherein the improvement in endothelial function is measurable after a single dosage of HDL.

12. The method of claim 1, consisting essentially of administering single dosage of reconstituted HDL sufficient for the acute improvement of endothelial function in a vascular disorder.

13. The method of claim 12, further comprising administering other therapeutic agents.

14. A method for reducing the risk of acute coronary disorders, comprising:
   administering an amount of reconstituted HDL which is sufficient for to reduce the risk of acute coronary disorders and which is sufficient for the acute improvement of endothelial cell function.

15. A method for treating vascular disorders for the acute improvement of endothelial function, comprising:
   administering a single dosage of reconstituted HDL which is sufficient for the acute improvement of endothelial function in a vascular disorder.

* * * * *

UNITED STATES PATENT AND TRADEMARK OFFICE
CERTIFICATE OF CORRECTION

PATENT NO. : 7,053,049 B2
APPLICATION NO. : 10/333212
DATED : May 30, 2006
INVENTOR(S) : Thomas F. Luescher It is certified that error appears in the above-identified patent and that said Letters Patent is hereby corrected as shown below:

On the Title page, Inventors: line 1, reads "Thomas Luescher," should read -- Thomas F. Luescher, --
On the front page, Assignee: reads "Bern (DE)" should read -- Bern (CH) --
Column 8, line 49, reads "apoliprotein) per mm" should read -- apolipoprotein per min --
Column 8, line 50, reads "10 mm" should read -- 10 min --
Column 8, line 59, reads "HDL" should read -- rHDL --
Column 8, line 61, reads "HDL" should read -- rHDL --
Column 8, line 62, reads "HDL" should read -- rHDL --
Column 8, line 64, reads "HDL" should read -- rHDL --
Column 8, line 67, reads "HDL" should read -- rHDL --
Column 9, line 10, reads "for to reduce" should read -- to reduce --

Signed and Sealed this

Twenty-fourth Day of April, 2007

JON W. DUDAS
*Director of the United States Patent and Trademark Office*